United States Patent [19]
Layton

[11] Patent Number: 5,658,353
[45] Date of Patent: Aug. 19, 1997

[54] METHOD FOR DONNING OR DOFFING AN ARTIFICIAL LIMB

[76] Inventor: Harry W. Layton, 7520 SW. Forest Ave., Lawton, Okla. 73505

[21] Appl. No.: 550,892

[22] Filed: Oct. 31, 1995

[51] Int. Cl.$^6$ .................................................. A61F 2/80
[52] U.S. Cl. .............................. 623/34; 623/33; 223/111
[58] Field of Search ................ 623/33–37; 223/111–113

[56] References Cited

U.S. PATENT DOCUMENTS

| | | |
|---|---|---|
| 708,685 | 9/1902 | White .................................. 623/37 |
| 1,996,377 | 4/1935 | Hinchen ............................... 223/111 |
| 2,464,443 | 3/1949 | Ganoe .................................. 623/36 |
| 2,533,404 | 12/1950 | Sharp et al. . |
| 2,569,790 | 10/1951 | White et al. . |
| 2,790,180 | 4/1957 | Hanser ................................. 623/34 |
| 4,128,903 | 12/1978 | Marsh et al. . |
| 5,007,937 | 4/1991 | Fishman et al. . |
| 5,139,523 | 8/1992 | Paton et al. ......................... 623/37 |
| 5,376,127 | 12/1994 | Swanson . |
| 5,376,131 | 12/1994 | Lenze et al. . |
| 5,549,709 | 8/1996 | Caspers ............................... 623/24 |

*Primary Examiner*—David H. Willse
*Attorney, Agent, or Firm*—Head, Johnson & Kachigian

[57] ABSTRACT

A method for donning or doffing a suction suspension prosthesis is disclosed. The air pressure between a residual limb and the distal end of a suction socket is electromechanically influenced to assist the donning or doffing of the suction socket. The air pressure is decreased to draw the residual limb into the suction socket and is increased to expel the residual limb from the suction socket. The method includes the use of a modified suction socket valve body, a low pressure vacuum pump, flexible tubing, and a non-greasy hypoallergenic lubricant.

11 Claims, 5 Drawing Sheets

METHOD FOR DONNING OR DOFFING AN ARTIFICIAL LIMB

TECHNICAL FIELD

The present invention relates generally to prosthetics, and, more specifically, to a method for donning or doffing a suction suspension prosthesis utilizing electromechanically adjusted differential air pressure.

BACKGROUND OF THE INVENTION

1. General Background

Broadly described, the field of prosthetics involves the replacement of missing body parts with artificial ones. Extremity prosthetics entails the substitution of an artificial limb for a lost extremity.

While many aspects of extremity prosthetics are critical to function, perhaps the most important aspect is suspension. The manner in which an artificial limb is suspended or attached to the residual limb determines the amount of control an amputee has over the prosthesis. The greater the weight and size of tissue loss due to amputation surgery, the more critical the method of suspension becomes. The method of suspension is particularly crucial to above-knee amputees, as above-knee amputations result in the largest percentage of amputees with the greatest amount of tissue loss.

Above-knee prostheses were originally suspended by some form of bulky strap or belt arrangement. The amputee would wear a sock on the residual limb to protect the skin tissue from the inner surface of the prosthesis, called the socket interface. The socket interface was usually made of wood and could irritate the skin, thus necessitating the use of the protective sock. The sock allowed the residual limb to easily slide into, as well as out of, the socket interface. This feature resulted in a fairly simple donning and doffing of the prosthesis. While this method of suspension is still applicable today, it has many well-known limitations and compromises.

Artificial limbs using suction sockets are now preferred. Suction sockets fit tightly around a patient's residual limb and are retained upon the residual limb by differential air pressure. An area of negative pressure between the residual limb and the distal end of a suction socket functions to hold the prosthesis upon the limb during use. This suspension method is the most advantageous for the amputee. It gives the amputee the ability to better control the prosthesis and provides for the greatest sensory or proprioceptive feedback. Suction suspension also makes a prosthesis feel lighter as compared to other forms of suspension. Since the introduction of suction as a viable means of suspension, it has found widespread use in virtually all levels of amputation.

Due to the numerous benefits associated with suction suspension, all amputees hope to gain the advantage of that form of suspension. Unfortunately, the amputees that are physically the least able to manage suction suspension are those who could benefit most from the advantages that suction suspension provides.

The problem lies in the donning (putting on) and doffing (taking off) of the suction socket. Donning and doffing a suction suspension prosthesis using conventional techniques is a rigorous affair too difficult for elderly, overweight, blind, arthritic, or muscularly weak patients to perform. Until now, the inability of these patients to don a suction socket prosthesis has denied them of its many advantages.

2. Conventional Donning Methods

Since the development of user-friendly suction socket fabrication techniques, this suspension method has been refined and adapted to many levels of extremity amputation. For purposes of illustration, the following discussion focuses on above-knee prosthetics, since this level of amputation best portrays the problems solved by the present invention. It must be understood, however, that the present invention is applicable to all suction suspension devices.

The combined development of removable air valves that seal against a freely machined insert in the distal end of a suction socket and donning techniques that allow an amputee to wear a prosthesis with no sock between their skin and the inner surface of the prosthesis resulted in a tremendous evolutionary step forward in prosthetic donning. The air valve allows for the creation and maintenance of an area of differential air pressure between a residual limb and the distal end of a suction socket, while a close fit between the walls of the socket and the residual limb skin maintains the integrity of the pressure differential. This pressure differential works to hold the prosthesis upon the limb. Many different valve and insert combinations have been made available, all having one thing in common—an opening of about one inch in diameter at the distal end of the socket that facilitates the use of a pull sock or bandage wrap to pull the residual limb into the socket of the prosthesis.

The donning techniques used in conjunction with pull socks and bandage wraps, however, require significant amputee balance, strength and mental acuity. In the case of a pull sock, the amputee pulls a tube stocking three feet long up the thigh to near groin level. The remaining length of this tube stocking material is hanging off of the residual limb. The hanging end of the stocking is inserted into the prosthesis at the trim line level and is pulled through the valve insert at the distal end of the socket to reduce slack in the pull sock. The amputee then stands on his sound leg and lets the residual limb, with the pull sock on, slip as far into the socket as it will easily slide. The amputee then again pulls slack out of the portion of the pull sock exposed through the valve housing. At this point the amputee is ready to begin the donning process that occurs as a result of controlled pulling on the free end of the residual limb just to the point that the pull sock begins to slip on the skin, at which point the residual limb is pulled a little deeper into the socket. This motion is repeated until the stocking is fully pulled through the valve housing and the amputee is able to see or feel with the end of the finger that the skin tissue is protruding into the valve housing. Once the amputee has reached this point, the valve body is installed which seals the suction so that they are free to ambulate.

The difference with the elastic bandage/wrap donning technique is that applying the elastic bandage wrap requires the ability to perform several circumferential wraps of the band around the residual limb with a generally even overlap of layers, beginning at the proximal end of the residual limb and continuing to the distal end and allowing the excess elastic wrap to dangle beyond the end of the limb. This loose end is then threaded through the prosthesis in the same fashion as the tube pull stocking. At this point the donning process is very similar to the tube stocking method. The amputee stands on the sound limb allowing the residual limb with the elastic wrap in place to slip into the socket of the prosthesis as far as it will easily slide, the slack in the band being pulled through the valve housing until the amputee begins to feel the bandage starting to slide against the skin, at which point they begin the delicate control process of firmly pulling the elastic bandage through the valve housing as they gradually let the limb be pulled deeper into the socket. At the same time they must proceed carefully, as the bandage might fold and roll itself in a fashion called "roping". As the wrap begins to rope it can burn the skin tissue if it is extricated too rapidly. The same type pumping motion as used with tube stocking is useful in relieving pressures or burning as a result of roping.

Both a tube pull sock and an elastic wrap require an amputee to have very good standing balance, hand grip strength, arm strength, sound side limb strength, vision, mental acuity, patience and peripheral sensory perception.

Many amputees began to learn that the success of an adequate suction suspension did not mean they had to rely on only two methods of donning. Suction suspension is dependant on compression of tissue, called an interference fit. This tissue compression is what requires the use of a pull sock to overcome the friction that results from an interference type of fit. The main reason to use a pull sock to overcome this interference fit is because of dry donning. Amputees began to realize that lubrication on their skin would allow the residual limb to more easily and quickly slide into the proper interference fit without the use of a tube sock or bandage wrap. However, this method also has its limitations. The amputee must be able to stand and balance on a sound side limb. The residual limb must be able to withstand the pressures put on it to force it into the socket. This source of pressure is referred to as sheer force. Sheer force occurs when tissue is pulled in two different directions at the same time. In this situation the skin in contact with the inner surface of the prosthetic socket is pulling in the opposite direction that the residual limb is moving. The lubrication medium reduces this pull but cannot eliminate it. This drag on the tissue pulls the flesh tight over the distal end of the residual limb, which is the area where the incision line is located. Consequently, the tissue of the residual limb is pulled tight over the cut end of the bone with tissue that is scarred as a result of amputation surgery. The resulting incision and scar tissue is less flexible than normal undamaged tissue. Due to these factors the wet donning method of suction suspension is limited to the minority of amputees that can stand and balance on one sound side limb and are able to tolerate the pressures applied to their residual limb from the resultant sheer forces associated with wet donning.

Another donning method to receive widespread use is the roll-on silicone interface that incorporates an extended metal pin that fits inside a receiver at the distal end of the prosthetic socket for securely engaging the extended pin. This roll-on silicone material is approximately three millimeters thick. With both hands, the amputee has to roll the side of the interface into a shape resembling a condom. Donning of the silicone interface is basically the same as donning a condom. The inverted roll of silicone is properly placed in position on the end of the residual limb and held in place securely while the sides are rolled up onto the flesh, being careful to avoid trapping of any air between the interface and the skin of the limb. The patient must also take care to maintain the proper position of the pin end of the interface. Once the silicon interface has been completely unrolled onto the limb, the amputee is ready to finish the donning procedure by pushing the limb with interface and locking pin into the socket of the prosthesis until the locking pin engages the receiver. The amputee has to stand to finish the donning procedure. Standing allows the limb interface combination to fully compress into the socket, resulting in full engagement of the locking pin into the receiver. This method has allowed a larger number of amputees to effectively use suction suspension but has required additional schooling for prosthestists to learn a revised suction socket fabrication technique as well as revised suction socket fitting procedures. Still, there remains the greatest majority of amputees that lack significant strength, balance and coordination to don a suction suspension prosthesis, but who could use such a prosthesis only if they could don the prosthesis properly.

All of the aforementioned conventional suction socket donning techniques continue to elude successful use by the greatest majority of amputees—the geriatric amputee patient and those with other physical or mental infirmities. Many persons are classified as nonviable suction users due to arthritis of the hands, wrists, elbows or shoulders, arthritis pain or weakness in the sound side limb, bilateral amputations, heart problems, visual impairments, balance problems, back or hip pain and weakness that makes bending over difficult, or other problems such as difficulty in learning to properly use conventional techniques. These persons are denied the many advantages of suction suspension and are forced to settle for a less desirable form of prosthesis suspension.

3. The Patent Art

United States patent references of interest include U.S. Pat. No. 2,533,404 to Sharp et al., U.S. Pat. No. 2,569,790 to Whim et al., and U.S. Pat. No. 5,376,131 to Lenze et al. While these patents show various suction sockets arrangements and valves therefor, each discloses a conventional manner of introducing a residual limb into the suction socket (see column 4, lines 55–64, of the Sharp patent; column 4, lines 47–56, of the White patent; and column 4, lines 42–61, of the Lenze patent).

It is thus an object of this invention to provide a method for donning or doffing a suction socket that makes the use of suction sockets available to those persons who, by reason of physical or mental infirmity, are not generally recognized as candidates for this type of prosthetic suspension.

SUMMARY OF THE INVENTION

The foregoing and other objects and advantages are attained by mechanically influencing the air pressure between a residual limb and the distal end of a suction socket, decreasing the air pressure to draw the residual limb into the suction socket and increasing the air pressure to expel the residual limb from the suction socket. This method of donning and doffing a suction socket is achieved using modified off-the-shelf componentry. A modified suction socket valve body, a low pressure vacuum pump, flexible tubing, and a non-greasy hypoallergenic lubricant are used in connection with the invention.

After developing a close suction fit through the use of transparent test socket fittings, the patient is introduced to the instant donning method. The use of the system is very straightforward. The modified valve body is installed into the suction socket housing. Flexible tubing is attached at one end to a nipple on the valve body and at the other end to the low pressure vacuum pump. The residual limb and/or socket is then lubricated to allow the vacuum of the pump to don the prosthesis.

The amputee positions the lubricated residual limb at the trim line of the prosthesis in such a manner as necessary to seal that opening to permit a vacuum to be initiated. With this position achieved, the vacuum pump is turned on. Donning occurs continuously and quite rapidly. Once the end of the residual limb has fully engaged the distal end of the suction socket, the modified valve is removed and a conventional valve is installed.

Doffing of the prosthesis occurs by installing the modified valve as before and connecting it to the vacuum pump, the air line from the vacuum pump having been reconfigured to provide a source of air rather than to draw air. Air is then injected into the distal end of the socket below the residual limb to push the limb from the socket.

Along with a modified conventional suction socket valve, a modified quick release valve is disclosed for use in connection with the present invention.

Still other objects and advantages of the present invention will become readily apparent to those skilled in this art from the following detailed description, wherein there is shown and described only the preferred embodiment of the invention, simply by way of illustration of the best mode contemplated for carrying out the invention. As will be realized, the invention is capable of modifications in various obvious respects, all without departing from the invention. Accordingly, the description should be regarded as illustrative in nature, and not as restrictive.

DETAILED DESCRIPTION OF THE PREFERRED EMBODIMENT

Figures 1, 2:
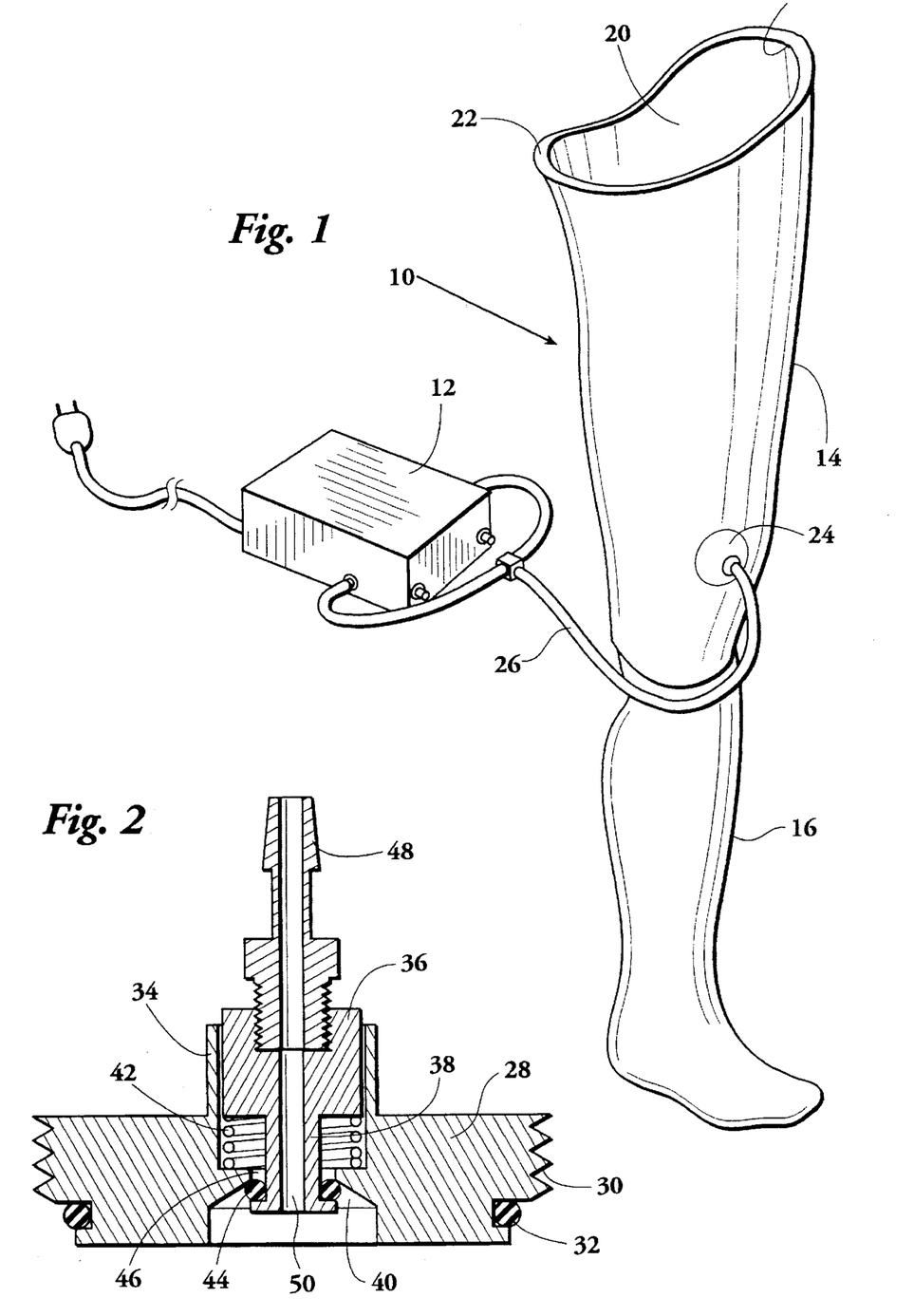
FIG. 1 is a perspective view of an above-knee prosthesis, a low pressure vacuum pump, and flexible tubing, all modified for use in connection with the present invention.
FIG. 2 is a cross section of a conventional suction socket valve body modified for use in connection with the present invention.

Shown in FIG. 1 is a conventional above-knee prosthesis, generally indicated by the reference numeral 10, connected to a low pressure vacuum pump 12. The prosthesis has an upper portion 14 and a lower portion 16. The upper portion 14 is known in the industry as a suction socket and will hereinafter be referred to as such 14.

The suction socket 14 is hollow, having a continuous circumferential interior wall 18. There is an opening 20 at the top or proximal end of the suction socket 14, the periphery of the opening being defined by a trim line 22. Shown at the distal end of the suction socket 14 is a modified suction socket valve body 24.

Shown connected to the modified suction socket valve body 24 is a piece of flexible tubing 26. The flexible tubing 26 runs between the modified suction socket valve body 24 and the low pressure vacuum pump 12.

Turning to FIG. 2 for further illustration, it should be understood that the modified suction socket valve body 24 is not a standard component on a conventional above-knee prosthesis 10. Though conventional prostheses often have a valve body located at the distal end of a suction socket, the standard valve body is not adapted for connection to a low pressure vacuum pump. Rather, focusing on FIG. 2, the standard suction socket valve body comprises a valve body 28 having threads 30 for threadable engagement with complementary threads tapped into a valve housing fabricated into the distal end of the suction socket 14. A sealing element 32, such as an O-ring, maintains fluid integrity between the interior of the suction socket 14 and the interface of the valve body 28 and the valve housing in the suction socket 14. The valve body 28 is manipulated by using an outwardly extending finger tab 34. A standard suction socket valve body also includes a valve body insert 36, which is positioned interior to the finger tab 34. The insert 36 has an insert stem 38 that traverses the valve body 28 to terminate in a frustoconical portion of a valve body bore 40. A spring 42 is positioned about the insert stem 38 and an O-ring 44 seals the annulus 46 that exists between the insert stem 38 and the wall of the frustoconical bore 40. Again, the above description relates to a conventional suction socket valve body, an example of which is the well-known Green Dot valve made by United States Manufacturing Co.

A standard suction socket valve body is not adapted to receive any type of air line fitting. The modifications made to a standard suction socket valve body for use in connection with the present invention include tapping the valve body insert 36 such as to provide threads for threadably engaging an air line barb fitting 48. The illustrated air line barb fitting 48 is manufactured by Small Parts, Incorporated. An airway 50 is also drilled through the valve body insert 36 for providing fluid communication between the interior of the suction socket 14 and the low pressure vacuum pump 12, which is connected by flexible tubing 26 to the air line barb fitting 48.

Thus, it can be appreciated that prior to the modification of a standard suction socket valve body, the conventional valve body is used merely as an access port for receiving pull socks, bandage wraps or the like as described above. Although a standard suction socket valve body may also be used to affect slight changes in suction by the pressing of the valve body insert 36, which would open the annulus 46 for a slight air movement, the standard suction socket valve body is not adaptable to a low pressure vacuum pump for the mechanical manipulation of differential air pressure.

The patient is introduced to the instant invention after developing a close suction fit through the use of transparent test socket fittings. After the patient has been provided with a correctly sized prosthesis 10, a modified valve body, such as illustrated in FIG. 2 or as hereinafter described, is installed into the distal end of the suction socket 14. The flexible tubing 26 is attached at one end to the air line barb fitting 48 and at the other end to the low pressure vacuum pump 12. The residual limb and/or interior wall of the suction socket 18 is then lubricated to allow the vacuum of the pump to don the prosthesis 10. The patient positions the lubricated residual limb at the trim line 22 of the prosthesis 10 in such a manner as necessary to seal the opening 20 to permit a vacuum to be initiated. The residual limb must circumferentially contact the interior wall of the suction socket 18 prior to vacuum donning. With this position achieved, the low pressure vacuum pump 12 is turned on. Donning occurs continuously and quite rapidly. Once the end of the residual limb is in full engagement with the distal end of the suction socket 14, the modified suction socket valve body 24 may be removed and a conventional valve installed.

The air pressure is preferably decreased to a negative pressure of about 70-120 mm (3-5 In.) Hg to draw the residual limb into the suction socket. It has been found that negative pressures in excess of 125 mm (5.5 In.) Hg create increasing amputee discomfort during the donning process. To expel the residual limb from the suction socket, air is introduced between the residual limb and the suction socket at a preferred pressure of about 3-5 psi and a preferred volume of about 60 to 110 cubic inches per minute.

The average length of time to don the prosthesis is dependent on residual limb size, lubrication used and overall socket tension. An 11 inch long above-knee residual limb with circumferences ranging from 19 inches at the proximal level to 13 inches at the distal measurement averages 45 to 50 seconds to achieve total contact.

An above-knee prosthesis can be donned using the present invention standing or sitting and probably even lying down. As compared to conventional techniques, the present invention is very user friendly. Amputees can easily control rotation of the prosthesis on the limb since they do not have to deal with conventional pumping motions or the considerable pressures associated with pushing or pulling on socks or bandage wraps. They also do not need to concern themselves with the extremely difficult task of maintaining balance in an upright position standing on one leg while bending over at the waist and hips trying to pull their tissue into the prosthesis.

The amputee will experience different physical sensations during the donning procedure due to the light negative pressure exerted on the tissues of the limb, as well as the constant motion of the prosthetic socket sliding onto the limb, seemingly under its own power. But the donning and doffing of the prosthesis in accordance with the invention is not painful or injurious.

Thus, the present invention makes suction socket suspension available to a vast array of amputees that never before have had the opportunity to experience this form of suspension due to the donning and doffing difficulties associated with conventional techniques. The invention is compatible in form and function with existing equipment. No change is required in suction socket design of fitting techniques. All that is required is to begin the process of expanding the use of suction sockets to include those amputees that had previously been classified as nonviable suction users.

Figure 3:
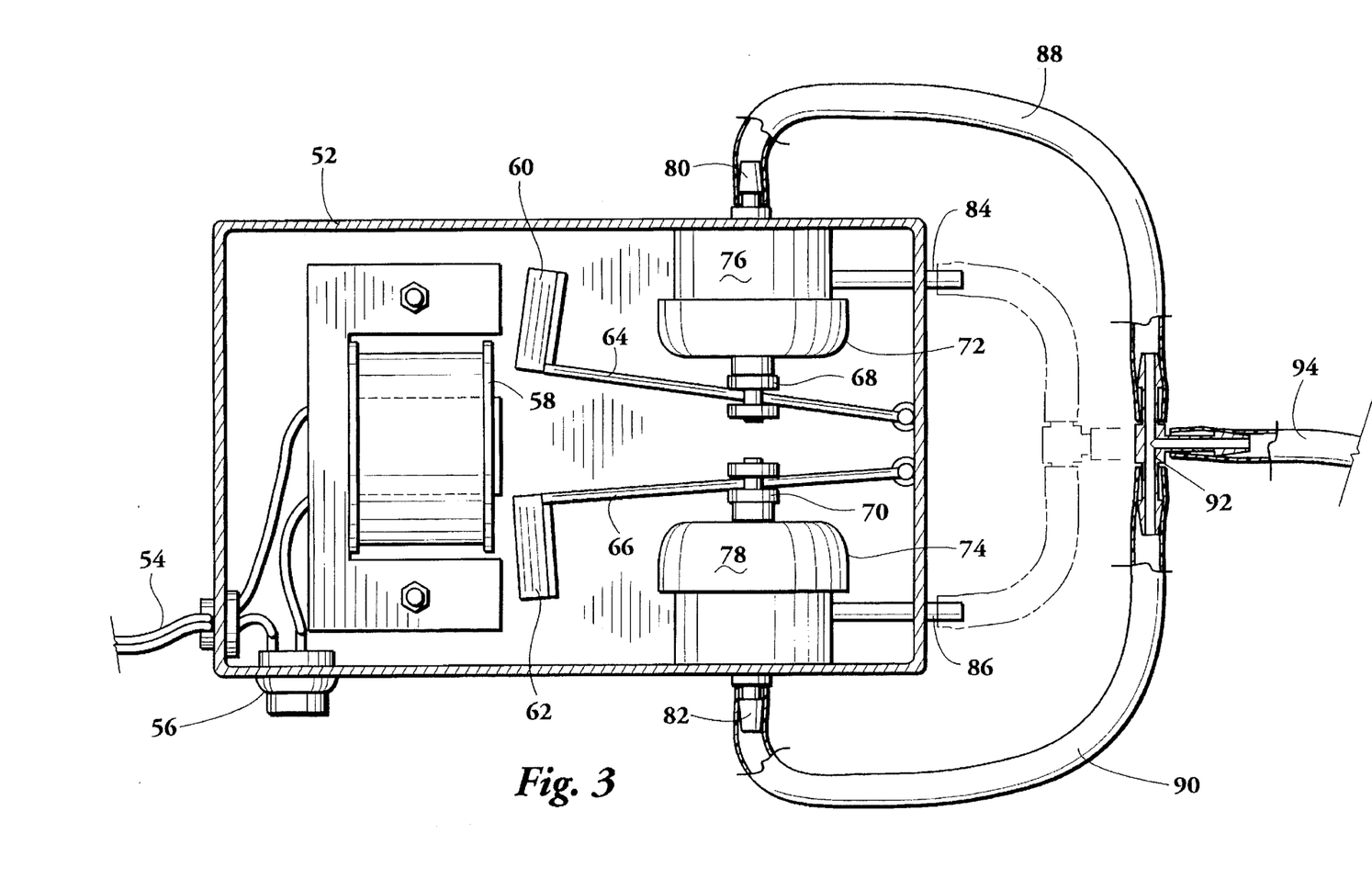
FIG. 3 is a cut-away top view of a low pressure vacuum pump modified for use in connection with the present invention.

The preferred embodiment of a low pressure vacuum pump 12 for use in connection with the present invention is illustrated in FIG. 3. The illustrated pump 12 is of the twin diaphragm variety. The pump 12 comprises a housing 52 within which is contained the working components of the pump 12. The pump illustrated is electrically powered via a power cord 54. A switch 56 is provided to initiate power to an electromagnet 58. The engagement of the electromagnet 58 causes lever magnets 60, 62 to vibrate. In turn, this vibration reciprocates arms 64, 66, respectively. The arms 64, 66 are connected by mounts 68, 70 to rubber pumps 72, 74. Each rubber pump 72, 74 is connected to a one-way reed valve 76, 78. Each reed valve 76, 78 has an associated air intake port 80, 82 and an exhaust port 84, 86.

The low pressure vacuum pump 12 of FIG. 3 is shown in its vacuum drawing configuration. A piece of flexible plastic tubing 88, 90 connects each air intake port 80, 82 to a barbed "T" fitting 92. A terminal piece of flexible tubing 94 then is used to connect the apparatus to the air line barb fitting (not shown in FIG. 3) on the modified suction socket valve body (not shown in FIG. 3).

It should be understood that the low pressure vacuum pump 12 illustrated in FIG. 3 and shown in general in FIG. 1 is merely one of numerous low pressure vacuum pumps capable of use in connection the present invention. What is shown is the preferred embodiment.

An alternative to modifying a standard suction socket valve body is the use of a quick release valve. The advantage in using a quick release valve is that the valve will not have to be installed and removed from the suction socket every time donning or doffing is required. A preferred embodiment of a quick release valve for use in connection with the present invention is illustrated in FIGS. 4-7.

Figure 4:
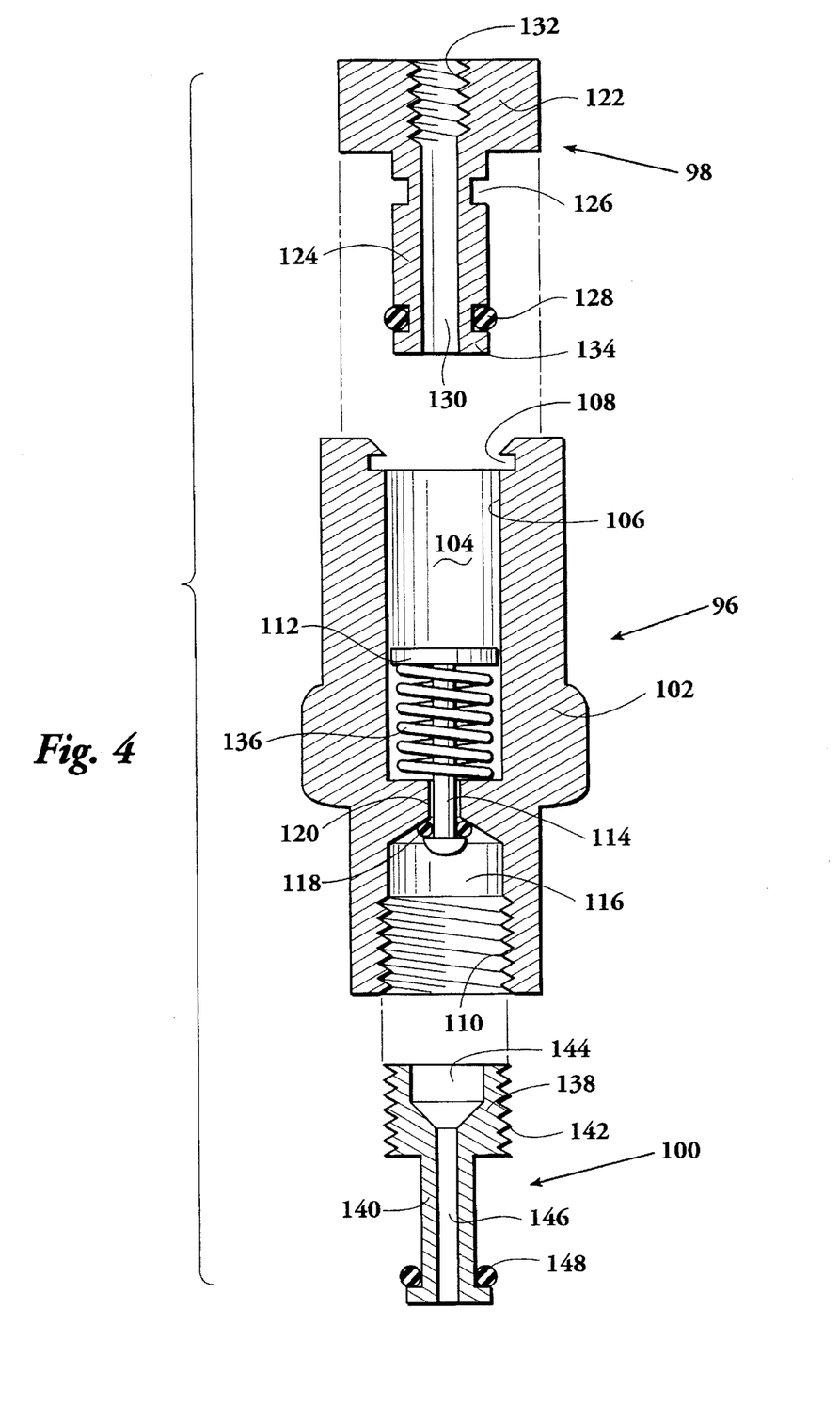
FIG. 4 is an exploded cross section of a quick release valve modified for use in connection with the present invention.

Turning to FIG. 4 a quick release valve body is generally indicated by the reference numeral 96. Other components illustrated are a quick release valve insert 98 and an adapter 100 for coupling the quick release valve body 96 to a standard suction socket valve body. The quick release valve body 96 and quick release insert 98 are off-the-shelf components, while the adapter 100 was specially made for use in connection with the present invention.

The quick release valve body 96 has a housing 102 through which is positioned a bore 104. The bore is defined by the inner wall 106 of the housing 102. The top of the housing 102 is provided with a machined groove 108, while the bottom of the housing 102 has been tapped and has internal threads 110. The bore 104 narrows between the upper and lower ends of the housing 102. A poppet valve 112 is positioned in the bore 104. The poppet valve stem 114 traverses the narrowed area of bore 104 to terminate in frustoconical area 116. An O-ring 118 seals the annulus 120 around the poppet valve stem 114.

The quick release valve insert 98 is adapted for insertion into the bore 104 of the quick release valve body 96. The quick release valve insert comprises a rectangular valve insert body 122 integrally connected to a valve insert stem 124. The top of the valve insert stem 124 is provided with a retainer groove 126, the purpose of which is explained below. An O-ring 128 is seated in a similar groove at the lower end at the valve insert stem 124. An airway 130 runs axially through the quick release valve insert 98. The upper end of the valve insert body 122 is tapped with threads 132 for receiving an air line barb fitting. When the quick release valve insert 98 is placed into the bore 104 of the quick release valve body 96, the insert surface indicated by the reference numeral 134 will abut the top surface of the poppet valve 112. If the quick release valve insert 98 is pressed downward into the bore 104 the poppet spring 136 will compress and the annulus 120 around the poppet valve stem 114 will be opened, as the O-ring 118 is moved away from the inner wall 106 of housing 102.

The adapter 100 includes a generally square adapter body 138 and an integrally formed adapter stem 140. The external surface of the adapter body 138 is provided with threads 142 complementary to the internal threads 110 of the quick release valve body 96. The interior of the adapter body 138 is provided with a frustoconical bore area 144, which leads to an airway 146 within the interior of the adapter stem 140. The lower end of the adapter stem 140 is provided with an O-ring 148.

Figure 5:
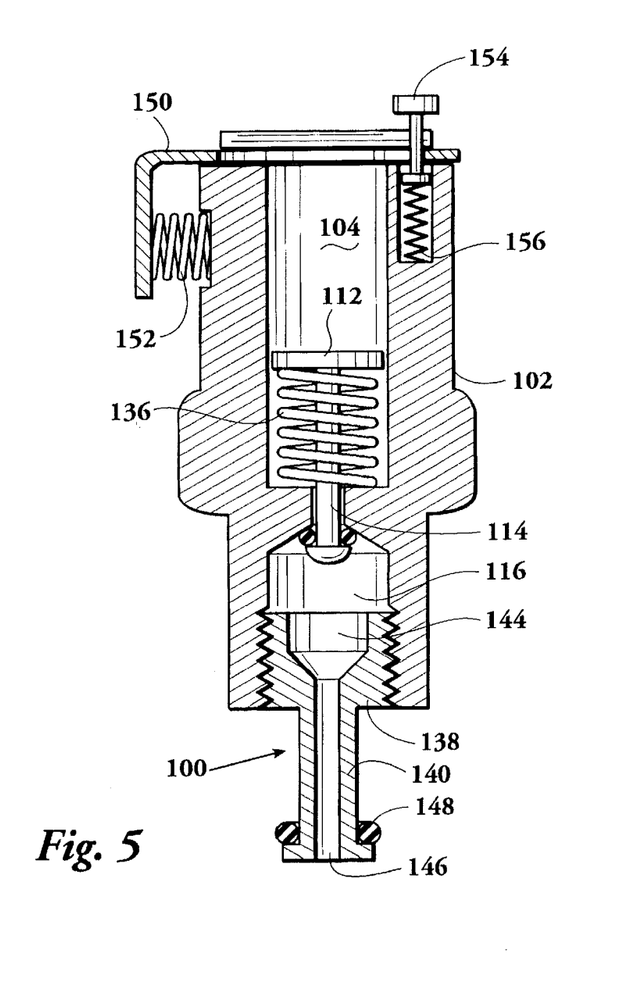
FIG. 5 is a cross section of a partially assembly modified quick release valve for use in connection with the present invention.

Turning now to FIG. 5, the quick release valve body 96 is shown in further detail with the adapter 100 threadably engaged therewith. The quick release valve insert 98 is not shown in FIG. 5. Accordingly, the poppet valve 112 is shown in its closed position. The focus in FIG. 5 is on the retention mechanism that holds the quick release valve insert 98 within the bore 104 of the housing 102. There is shown within the machined groove 108 an insert retainer 150. The insert retainer 150 is downwardly deflected at one end, under which end is provided an insert retainer spring 152. The insert retainer spring 152 can be compressed by thumb pressure to slide insert retainer 150 within the machined groove 108. At the side of the housing 102 opposite that of insert retainer spring 152 there is provided a retainer pin 154. The retainer pin 154 is supported upon a retainer pin spring 156.

Figure 6:
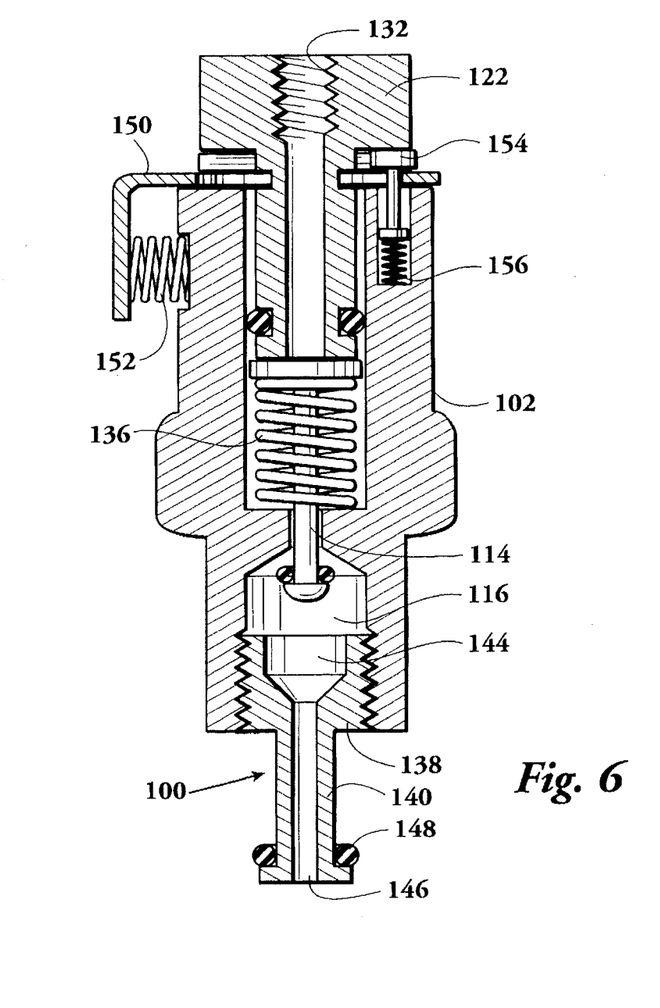
FIG. 6 is a cross section of a fully assembled modified quick release valve for use in connection with the present invention.

Turning now briefly to FIG. 6, there is shown the quick release valve body 96 threadably engaged with the adapter 100, the quick release valve insert 98 having been inserted into the bore 104 of the housing so as to compress the poppet spring 136 and open the annulus 120 around the poppet valve stem 114. This view illustrates that the quick release valve insert 98 is held within the bore 104 of the housing 102 by the action of the insert retainer 150 filling the retainer groove 126. In this position air can be moved throughout the apparatus.

Figure 7A:
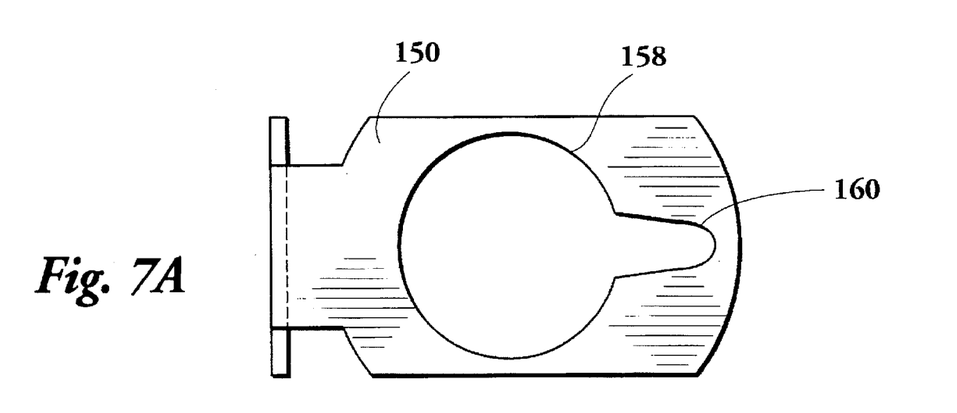
FIG. 7A is a top view of an insert retainer used in connection with the modified quick release valve.
Figure 7B:
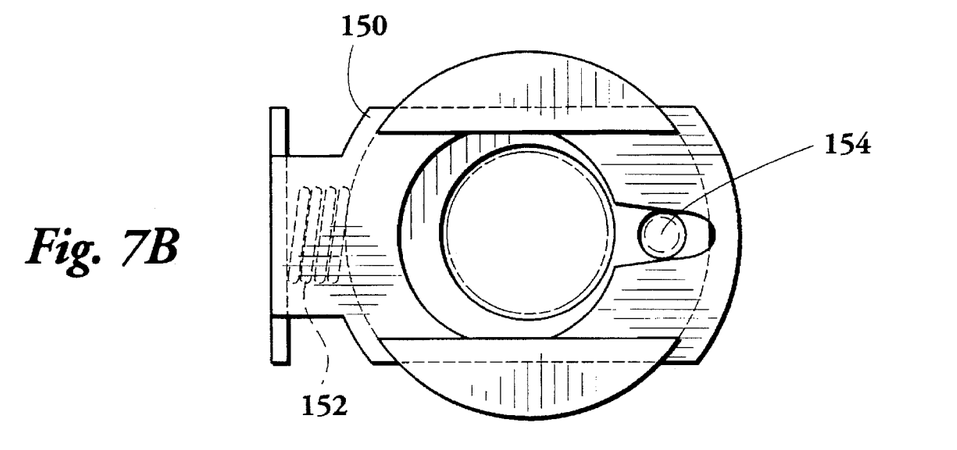
FIG. 7B is a top view of the insert retainer of FIG. 7A as installed in a quick release valve body and shown in its compressed or open position.
Figure 7C:
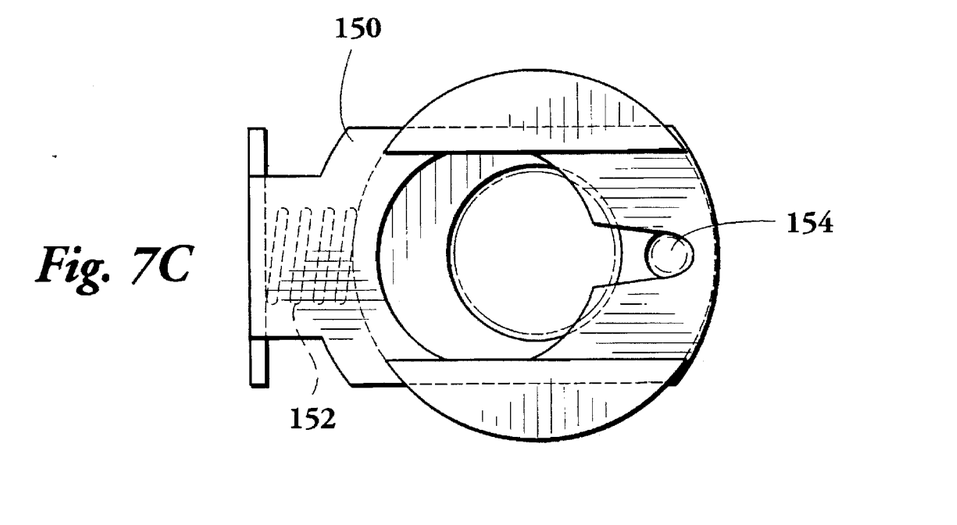
FIG. 7C is a top view of the insert retainer of FIG. 7A as installed in a quick release valve body and shown in its free or closed position.

FIGS. 7A–7C show more distinctly the function of the insert retainer 150. The insert retainer itself is shown in FIG. 7A as having an insert retainer bore 158 and a retainer pin notch 160. Tuning to FIG. 7B the insert retainer 150 is shown as seated in the machined groove 108 of the housing 102 of the quick release valve body 96. The insert retainer spring 152 is shown to be compressed. This compression results in the insert retainer bore 158 being moved toward the retainer pin 154. This allows for the insertion of the quick release valve insert 98 into the quick release valve body 96. As shown in FIG. 7C, after the quick release valve insert 98 has been introduced into the quick release valve body 96, pressure is removed from the downwardly deflected portion of insert retainer 150 so that the insert retainer spring 152 is decompressed. This causes the insert retainer bore to move toward the insert retainer spring 152. Consequently, retainer pin notch 160 moves to abut the retainer pin 154. A portion of the periphery of the insert retainer bore 158 catches the retainer groove 126 to maintain the position of the quick release valve insert 98 within the quick release valve body 96.

While the invention has been described with a certain degree of particularity, it is manifest that many changes may be made in the method hereinabove described without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A method for donning and doffing a suction suspension prosthesis, said prosthesis including a suction socket having an open proximal end for receiving a residual limb and a distal end, comprising influencing air pressure between said residual limb and said distal end of said suction socket, decreasing the air pressure to a negative pressure to draw said residual limb into said suction socket and increasing the air pressure to a positive pressure to expel said residual limb from said suction socket.

2. The method according to claim 1, further comprising lubricating said residual limb prior to insertion of said residual limb into said suction socket.

3. The method according to claim 1, wherein the air pressure is decreased to a negative pressure of about 70–120 mm (3–5 In.) Hg to draw said residual limb into said suction socket.

4. The method according to claim 1, wherein air is introduced between said residual limb and said distal end of said suction socket at a pressure of about 3–5 psi and a volume of about 60 to 110 cubic inches per minute to expel said residual limb from said suction socket.

5. A method for donning a suction suspension prosthesis, said prosthesis including a suction socket having an open proximal end for receiving a residual limb and a distal end, comprising:

(a) installing a valve means into said distal end of said suction socket, said valve means engaging a first end of a piece of flexible tubing;

(b) lubricating said residual limb to obtain a lubricated limb;

(c) positioning said lubricated limb into said open proximal end of said suction socket such that said lubricated limb circumferentially contacts an upper, interior portion of said suction socket; and (d) drawing air through a second end of said flexible tubing by means of a low pressure vacuum pump to create a negative air pressure between said residual limb and said distal end of said suction socket such that said residual limb is pulled into full engagement within said suction socket.

6. The method according to claim 5, wherein the air pressure is decreased to a negative pressure of about 70–120 mm (3–5 in.) Hg to draw said residual limb into said suction socket.

7. The method according to claim 5, wherein said valve means comprises a quick release valve for connection to a valve body.

8. The method according to claim 7, wherein said quick release valve is connected to said valve body by use of an adapter, said adapter having an adapter body for threadable coupling to said quick release valve, a stem for traversing said valve body, a sealing element circumferentially positioned about said stem, and an airway for fluid communication between said quick release valve and said valve body.

9. The method according to claim 5, wherein said low pressure vacuum pump comprises a twin diaphragm vacuum pump.

10. A method of doffing a suction suspension prosthesis, said prosthesis including a suction socket having a proximal end in which is received a residual limb and a distal end, comprising:

(a) installing a valve means into said distal end of said suction socket, said valve means engaging a first end of a piece of flexible tubing;

(b) introducing air through a second end of said flexible tubing to create a positive air pressure between said residual limb and said distal end of said suction socket such that said residual limb is pushed out of said suction socket.

11. The method according to claim 10, wherein air is introduced between said residual limb and said suction socket at a pressure of about 3–5 psi and a volume of about 60 to 110 cubic inches per minute to expel said residual limb from said suction socket.

\* \* \* \* \*